United States Patent
Cedergreen

(10) Patent No.: US 8,335,695 B2
(45) Date of Patent: Dec. 18, 2012

(54) PHARMACEUTICAL PRICING METHOD

(75) Inventor: Jacob Cedergreen, St. Louis, MO (US)

(73) Assignee: Express Scripts, Inc., St. Louis, MO (US)

(*) Notice: Subject to any disclaimer, the term of this patent is extended or adjusted under 35 U.S.C. 154(b) by 381 days.

(21) Appl. No.: 12/313,131

(22) Filed: Nov. 17, 2008

(65) Prior Publication Data

US 2009/0313039 A1    Dec. 17, 2009

Related U.S. Application Data

(60) Provisional application No. 61/003,326, filed on Nov. 16, 2007.

(51) Int. Cl.
*G06Q 50/00* (2012.01)
(52) U.S. Cl. .......................................................... 705/2
(58) Field of Classification Search .................. 705/2, 3
See application file for complete search history.

(56) References Cited

U.S. PATENT DOCUMENTS

| | | | |
|---|---|---|---|
| 2001/0037216 A1 | 11/2001 | Oscar et al. | |
| 2002/0002473 A1* | 1/2002 | Schrier et al. | 705/3 |
| 2004/0117323 A1 | 6/2004 | Mindala | |
| 2004/0243438 A1 | 12/2004 | Mintz | |
| 2006/0116905 A1 | 6/2006 | Yered | |
| 2006/0184391 A1* | 8/2006 | Barre et al. | 705/2 |
| 2006/0277064 A1* | 12/2006 | Cannata | 705/2 |
| 2007/0050209 A1 | 3/2007 | Yered | |
| 2007/0067218 A1 | 3/2007 | Bingham | |
| 2007/0233516 A1* | 10/2007 | Howe et al. | 705/2 |

* cited by examiner

*Primary Examiner* — Gerald J. O'Connor
*Assistant Examiner* — Neha Patel
(74) *Attorney, Agent, or Firm* — Bryan Cave LLP

(57) ABSTRACT

This invention provides for innovative methods of pricing generic drugs. In a preferred embodiment, wholesale acquisition costs of identified comparable brand drugs for the generic drugs to be priced according to the invention are identified as comparable brand drug values. The comparable brand drug values are averaged to calculate a stable, predictable benchmark value to be used to determine the price of the generic drug, according to methods of this invention.

16 Claims, 3 Drawing Sheets

PHARMACEUTICAL PRICING METHOD

RELATED APPLICATION INFORMATION

This application claims the benefit of U.S. Provisional Patent Application Ser. No. 61/003,326, filed on Nov. 16, 2007, the disclosure of which is incorporated herein by reference in its entirety for all purposes.

FIELD OF THE INVENTION

This invention relates generally to pricing pharmaceuticals; specifically, to methods of pricing generic drugs, to methods of creating tools to be used in pricing generic drugs, and to tools used in the pricing of generic drugs.

BACKGROUND OF THE INVENTION

Determining the price of a drug can be relevant for a variety of purposes. Historically, a price of a drug has been determined based on a benchmark called the "average wholesale price." The average wholesale price, or "AWP", is established and published by First Data Bank based on information it receives from wholesalers of drugs. However, AWP may not continue to be a reliable and/or readily available benchmark for pricing generic drugs; accordingly, methods and systems for pricing drugs based on AWP as a benchmark may no longer be effective for determining a price of a generic drug. Therefore, a need exists for new and innovative methods and pricing generic drugs.

BRIEF SUMMARY OF THE INVENTION

An invention having various embodiments that meet these needs has now been developed. Embodiments of the present invention include methods for determining the price of a generic drug based on a benchmark calculated based on one or more identified comparable drug value of an identified comparable drug.

In one aspect, this the invention concerns a computer-implemented method for determining the price of a generic drug, the method comprising the steps: (a) receiving information about the generic drug; (b) identifying a comparable brand drug for the generic drug based on the received information; (c) identifying a comparable brand drug value for the comparable brand drug; (d) calculating a benchmark value for the generic drug based on the comparable brand drug value; (e) determining the price of the generic drug based on the benchmark value; and (f) providing the determined price of the generic drug.

In another aspect, this the invention concerns a computer-implemented method for determining the price of a generic drug, the method comprising the steps: (a) receiving information about the generic drug; (b) receiving information about the payee; (c) identifying a comparable brand drug for the generic drug based on the received generic drug information; (d) identifying a comparable brand drug value for the comparable brand drug; (e) calculating a benchmark value for the generic drug based on the comparable brand drug value; (f) determining the price of the generic drug based on the benchmark value and the received payee information; and (g) providing the determined price of the generic drug.

In yet another aspect, a computer-implemented method for determining the price of a generic drug comprises the steps: (a) receiving information about the generic drug; (b) receiving information about the payee; (c) identifying a comparable brand drug for the generic drug based on the received generic drug information, wherein the comparable brand drug is a bioequivalent of the generic drug; (d) identifying at least two comparable brand drug values for the comparable brand drug wherein each comparable brand value for the drug comprises a wholesale acquisition cost of the comparable brand drug; (e) calculating a benchmark value for the generic drug based on the comparable brand drug value, wherein the benchmark value comprises an average of the comparable brand drug values; (f) determining the price of the generic drug based on the benchmark value and the received payee information; and (g) providing the determined price of the generic drug.

Embodiments of the present invention can provide one or more of the above-described features and one or more of the above-described benefits to parties interested in determining the price of a generic drug. Still other features and benefits will be apparent to those skilled in the art.

BRIEF DESCRIPTION OF THE FIGURES

The invention will be better understood from a reading of the following detailed description, taken in conjunction with the accompanying Figures in which.

DETAILED DESCRIPTION OF THE INVENTION

Price of a Drug

Figure 1:
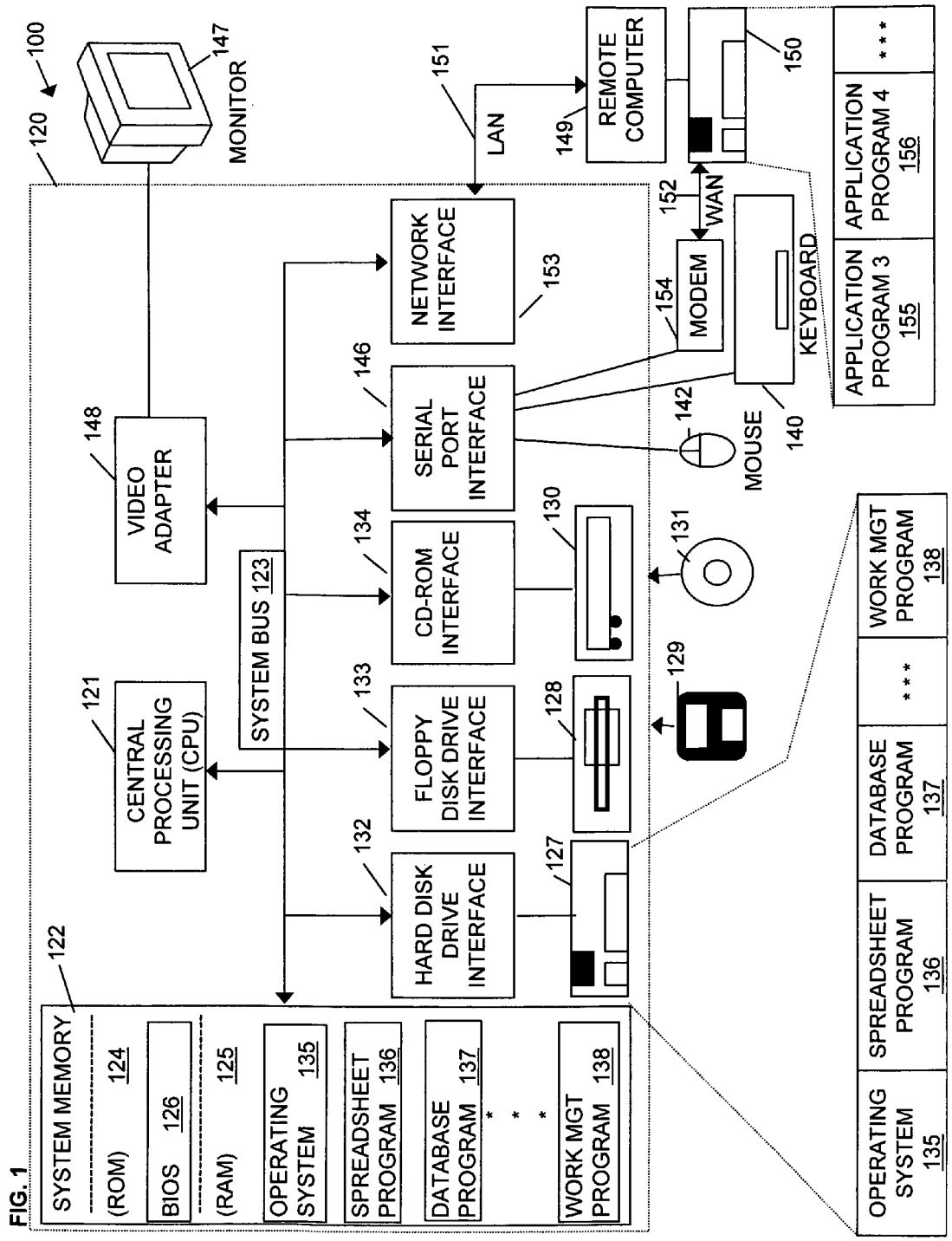
FIG. 1 illustrates an exemplary operating environment for implementation of various embodiments of the invention.

There are a variety of situations in which it may be desirable to determine a price, cost, value, or other measure of the worth or relative worth (the "price") of a drug. For example:

A direct employer, managed care organization, third party administrator, purchasing coalition, or labor union (referred to herein as a "plan") may pay a price to a pharmaceutical benefit manager ("PBM") for a drug dispensed to a participant in the plan.

A PBM may pay a price for a drug to the pharmacy that dispenses that drug to a participant in a plan.

A PBM may pay a price for a drug to the manufacturer of the drug.

A health care provider who receives a drug from a PBM, acting as a distributor, may pay a price for that drug to the PBM.

A pharmacy may pay a price for a drug to a wholesaler.

A pharmacy may pay a price for a drug to a manufacturer.

A patient who receives a drug from a pharmacy may pay a price for the drug to the pharmacy.

Furthermore, it may be relevant to determine the price of a drug in situations that may be more indirectly related to a sale of the drug between parties. For example, the price of a drug may be relevant for purposes of: (1) determining whether a particular drug should be included on a formulary, (2) determining the preferred placement of a drug in a step therapy treatment protocol, (3) evaluating drug treatment options for a particular condition, (4) selecting among drugs in a therapy class, (5) evaluating whether the drug would benefit from more specialized distribution, administration, support, etc. (e.g., whether the drug would be well-suited to be dispensed via a specialty pharmacy), and/or (6) determining a co-pay for the drug.

"Price" may refer to a price per unit (e.g., per tablet, capsule, milliliter [or other appropriate measure for a drug provided in liquid form]); a price per a designated period, such as the price for a 30-day supply (wherein the amount needed for a 30-day supply [or another designated period] could be the amount needed by a particular patient during a 30-day period based on the patient's specific dosage requirements or it could be based on an average or otherwise standardized determination of the amount needed for a typical 30-day period); or a price per measure of active ingredient (e.g., per milligram of active ingredient). The determined "price" of a drug may be expressed a fixed value, e.g., as a specific dollar amount; alternatively the determined "price" of a drug may be expressed as a relative value, e.g., in reference to one or more other drugs. Thus, the determined price of a first drug may be "$10 less, per unit" than a second drug. It will be understood by those with skill in the art that a single drug may have more than one price; for example, the drug may have a first price when the price is determined in reference to a first payee and a second price when determined in reference to a second payee.

The methods and systems of the present invention are directed to methods and systems of determining a price of a generic drug. The term "generic drug" is understood in the art and typically refers to a drug for which there is no current patent protection in the relevant jurisdiction. Using the United States as an example, a generic drug is a drug, the use, manufacture, sale, or offer of sale of which would not infringe a valid claim of an in-force United States patent.

As noted above, historically, a price of a generic drug has been determined based on AWP as a benchmark. However, since AWP may not continue to be a reliable and/or readily available benchmark for pricing generic drugs, methods and systems for pricing drugs based on AWP as a benchmark may no longer be effective for determining a price of a generic drug. Therefore, a need exists for new and innovative methods and systems for pricing generic drugs.

This invention provides new and innovative methods and systems for pricing generic drugs, which methods and systems provide reliable, stable pricing for generic drugs. Preferably, the methods and systems of this invention are computer-implemented.

Exemplary Operating Environment

FIG. 1 is a block diagram illustrating an exemplary operating environment for implementation of various embodiments of this invention. The exemplary operating environment 100 includes a general-purpose computing device in the form of a conventional personal computer 120. Generally, the personal computer 120 includes a processing unit 121, a system memory 122, and a system bus 123 that couples various system components including the system memory 122 to the processing unit 121. The system bus 123 may be any of several types of bus structures including a memory bus or memory controller, a peripheral bus, and a local bus using any of a variety of bus architectures. The system memory includes a read-only memory (ROM) 124 and a random access memory (RAM) 125. A basic input/output system (BIOS) 126, containing the basic routines that help to transfer information between elements within personal computer 120, such as during start-up, is stored in ROM 124.

Personal computer 120 further includes a hard disk drive 127 for reading from and writing to a hard disk, not shown, a magnetic disk drive 128 for reading from or writing to a removable magnetic disk 129, and an optical disk drive 130 for reading from or writing to a removable optical disk 131 such as a CD-ROM or other optical media. Hard disk drive 127, magnetic disk drive 128, and optical disk drive 130 are connected to system bus 123 by a hard disk drive interface 132, a magnetic disk drive interface 133, and an optical disk drive interface 134, respectively. Although the exemplary environment described herein employs hard disk 127, removable magnetic disk 129, and removable optical disk 131, it should be appreciated by those skilled in the art that other types of computer readable media which can store data that is accessible by a computer, such as magnetic cassettes, flash memory cards, digital video disks, RAMs, ROMs, and the like, may also be used in the exemplary operating environment. The drives and their associated computer readable media provide nonvolatile storage of computer-executable instructions, data structures, program modules, and other data for personal computer 120.

A number of program modules may be stored on hard disk 127, magnetic disk 129, optical disk 131, ROM 124, or RAM 125, including an operating system 135, a spreadsheet program 136, and a database program 137. Program modules include routines, sub-routines, programs, objects, components, data structures, etc., which perform particular tasks or implement particular abstract data types.

A user may enter commands and information into personal computer 120 through input devices, such as a keyboard 140 and a pointing device 142. Pointing devices may include a mouse, a trackball, and an electronic pen that can be used in conjunction with an electronic tablet. Other input devices (not shown) may include a microphone, joystick, game pad, satellite dish, scanner, or the like. These and other input devices are often connected to processing unit 121 through a serial port interface 146 that is coupled to the system bus 123, but may be connected by other interfaces, such as a parallel port, game port, a universal serial bus (USB), or the like. A display device 147 may also be connected to system bus 123 via an interface, such as a video adapter 148. In addition to the monitor 147, personal computers typically include other peripheral output devices (not shown), such as speakers and printers.

The personal computer 120 may operate in a networked environment using logical connections to one or more remote computers 149. Remote computer 149 may be another personal computer, a server, a client, a touter, a network PC, a peer device, or other common network node. While a remote computer 149 typically includes many or all of the elements described above relative to the personal computer 120, only a memory storage device 150 has been illustrated in FIG. 1. The logical connections depicted in FIG. 1 include a local area network (LAN) 151 and a wide area network (WAN) 152. Such networking environments are commonplace in offices, enterprise-wide computer networks, intranets, and the Internet.

When used in a LAN networking environment, the personal computer 120 is often connected to the local area network 151 through a network interface or adapter 153. When used in a WAN networking environment, the personal computer 120 typically includes a modem 154 or other means for establishing communications over WAN 152, such as the Internet. Modem 154, which may be internal or external, is connected to system bus 123 via serial port interface 146. In a networked environment, program modules 155, 156 or portions thereof, depicted relative to remote computer 149, may be stored in the remote memory storage device 150. It will be appreciated that the network connections shown are exemplary and other means of establishing a communications link between the computers may be used.

Moreover, those skilled in the art will appreciate that the present invention may be implemented in other computer system configurations, including hand-held devices, multiprocessor systems, microprocessor based or programmable consumer electronics, network personal computers, mini-computers, mainframe computers, and the like. The invention may also be practiced in distributed computing environments, where tasks are performed by remote processing devices that are linked through a communications network. In a distributed computing environment, program modules may be located in both local and remote memory storage devices.

Calculating a Benchmark Value

There are a variety of sources of information about drug cost. For example:

Average Wholesale Price. The Average Wholesale Price, or "AWP", is established and published by data providers, e.g., First DataBank, Inc. and Medi-Span (a part of Wolters Kluwer Health), based on information received from wholesalers of drugs. As noted above, a drug's AWP has traditionally served as benchmark for determining the price of that drug.

Brand Wholesale Acquisition Cost The Brand Wholesale Acquisition Cost, or "Brand WAC", is set by manufacturers of brand drugs (as discussed in more detail below), at least annually. A brand drug's Brand WAC has been used as a benchmark in pricing sales of that drug between a brand manufacturer and its wholesalers. A brand manufacturer will often pay careful attention to its Brand WAC for a particular drug, because the Brand WAC of one drug relative to the Brand WAC of another may help set the market positioning of the particular drug.

Generic Wholesale Acquisition Cost. Although the name is similar, Generic Wholesale Acquisition Cost ("Generic WAC") is not the generic drug equivalent of the Brand WAC. As an initial matter, fifteen to twenty percent of generic drugs do not have a Generic WAC. Furthermore, for those generic manufacturers that do set a Generic WAC, it is not updated as frequently. Finally, it is not, within the industry, a common benchmark for pricing sales of drugs and it is understood to have little or no correlation with the actual cost of the generic drug.

As a part of the federal government's new drug prescription programs for Medicare and Medicaid, it will require all drug manufacturers to publish the Average Manufacturer's Price, or "AMP", for its drugs (generic and brand). This information will be published by the Center for Medical Services ("CMS"). The AMP of a drug will be the true average price received by the manufacturer for that drug, taking into account subsequently-paid rebates, i.e., it is to be the true "average cost."

The above-described information, and sources of such information, will be familiar to those with ordinary skill in the art. Furthermore, those with ordinary skill in the art will recognize that other terms may be used to describe this information, and that other information about the value of particular drug may become available in the future.

Another aspect of drug pricing may be rebates. Rebates are often provided by a drug manufacturer to a PBM, wholesaler, distributor or other participant in the distribution chain. Rebates may be factored into pricing in a variety of ways. For example, a manufacturer may provide rebates to a PBM based on actual sales of its drug. The PBM may pass on all or a portion of this rebate to its client. A formulary rebate may be provided by a manufacturer to a PBM based on the position of the manufacturer's drug on the PBM's formulary. Again, this rebate may be passed on, in whole or in part, to the client.

There are a variety of methods of determining the price of the drug; the preferred method may depend upon the identity of the payor, the payee, and/or the purpose for which the price is determined. For example, assuming an AWP for a drug of $2 per unit, the price of 30 unit supply of a drug (sometimes referred to in the art as the "ingredient cost") may be calculated as follows:

| | |
|---|---|
| AWP for the drug ($2 × 30): | $60 |
| Contract Discount: | −10% (i.e., −$6) |
| Dispensing Fee: | +$2 |
| Net Client Rate: | $56 |
| Less Co-Pay: | −$10 |
| Total Paid by Client: | $46 |

As noted above, AWP may not continue to be a reliable and/or readily available benchmark for pricing. Therefore, a need exists for new and innovate methods and tools for pricing generic drugs.

For brand drugs, the inventor discovered that a brand drug's Brand WAC may provide an acceptable alternative to AWP as a benchmark for that drug.

Discovery of a new benchmark for generic drugs proved to be even more challenging. For example, the inventor discovered that using the Generic WAC of a generic drug may be an unacceptable pricing benchmark for that for a variety of reasons, including but not limited to the following: (1) it is unavailable for approximately twenty percent of generic drugs, (2) AWP (the traditional benchmark) has no relationship to Generic WAC, and (3) Generic WACs decrease over time and then stabilize at an unpredictable stabilization point relative to either AWP or acquisition price.

This invention provides for novel methods of determining the price of a generic drug that comprise identifying a comparable brand drug for the generic drug, identifying a comparable brand drug value for the comparable brand drug, calculating a benchmark value for the generic drug based on the comparable brand drug value, and determining the price of the generic drug based on the benchmark value.

The term "brand drug" generally refers to an "innovator drug", as such term is used in the art; specifically, a drug originally marketed under an original new drug application approved by the Food and Drug Administration. See Section 1927(k)(7)(A)(ii) of the Social Security Act. The "manufacturer" of a drug is generally defined by reference to the definition of the term "manufacturer" currently found at Section 1927(k)(5) of the Social Security Act. Specifically, Section 1927(k)(5) of the Social Security Act defines "manufacturer" as:

any entity which is engaged in (A) the production, preparation, propagation, compounding, conversion, or processing of prescription drug products, either directly or indirectly by extraction from substances of natural origin, or independently by means of chemical synthesis, or by a combination of extraction and chemical synthesis, or (B) in the packaging, repackaging, labeling, relabeling, or distribution of prescription drug products.

A brand drug and its manufacturer are typically designated in materials published by the Centers for Medicare and Medical Services. Thus, using these terms of art, the "Brand WAC" of a particular drug typically would be the wholesale acquisition cost of an innovator drug provided by the manufacturer of that drug.

As noted above, this invention comprises identifying a comparable brand drug of the generic drug to be priced according to a method or system of this invention. A "comparable brand drug" of a generic drug should be broadly understood and refers to a brand drug that is the pharmaceutical equivalent of the generic drug, bioequivalent of the generic drug, a pharmaceutical alternative of the generic drug, in the same therapeutic class, therapeutic category, or pharmacological class as the generic drug, and/or otherwise pharmaceutically comparable to the generic drug.

At 21 C.F.R. 320.1, the U.S. Food and Drug Administration (FDA) defines "pharmaceutical equivalents," in pertinent part, as "drug products in identical dosage forms that contain identical amounts of the identical active ingredient." "Pharmaceutical alternatives" are defined, in part, as "drug products that contain the identical therapeutic moiety, or its precursor, but not necessary in the same amount or dosage form or as the same salt or ester." Finally, "bioequivalence" is defined in part as "the absence of a significant difference in the rate and extent to which the active ingredient or active moiety in pharmaceutical equivalents or pharmaceutical alternatives becomes available at the site of drug action when administered at the same molar dose under similar conditions in an appropriately designed study."

As understood by those with skill in the art, and a drug may be characterized by its therapeutic class, therapeutic category, and/or pharmacological class (generally, its "therapeutic class"). Therapeutic class may refer to a condition a drug is used to treat and/or the mode of therapeutic action. The therapeutic class of a drug may be defined differently depending upon the desired level of specificity. For example, the therapeutic class of a drug may be "anticonvulsant" or it may be "calcium channel modifying agent," depending upon the desired degree of specificity. Other examples of therapy class include heart and circulatory drugs and the more specific angiotensin converting enzyme inhibitors; gastrointestinal agents and the more specific proton pump inhibitors; and immunological agents, the more specific immune stimulants, and the even more specific vaccines to prevent diphtheria.

A comparable brand drug may be identified for a generic drug to be priced according to a method of this invention may be identified by one or more individuals skilled in the pharmaceutical arts (e.g., a pharmacist, a physician, a nurse, or other person with sufficient knowledge of drugs to make a skilled determination—a "skilled individual") based, at least in part, upon his or her understanding of a comparison of the generic drug to available brand drugs. Identifying a comparable brand drug for a generic drug may be accomplished by a single skilled individual and/or by more than one skilled individual. A group of skilled individuals may work together to identify a comparable brand drug for a generic drug by consensus.

Figure 2:
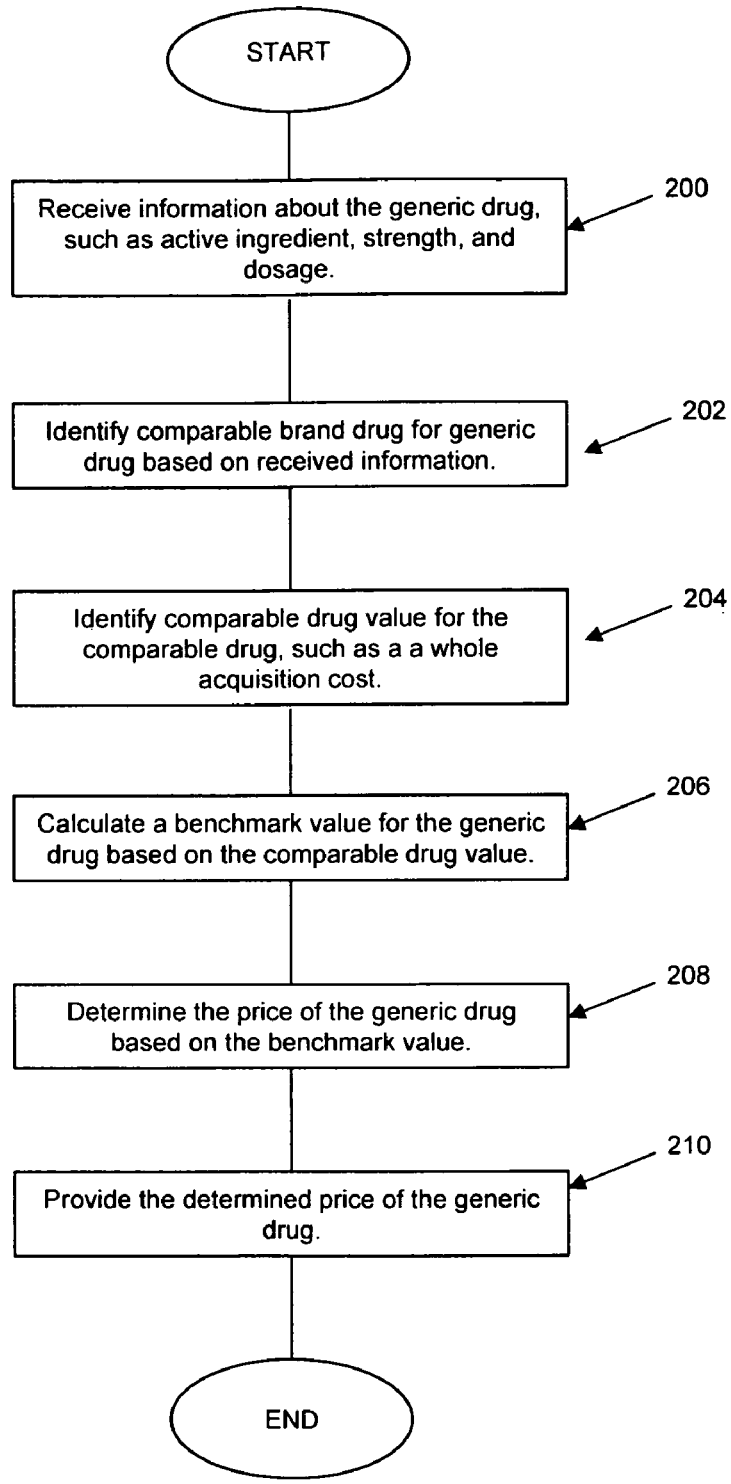
FIG. 2 is a flowchart illustrating an embodiment of a method of the invention.

In a preferred computer-implemented embodiment of this invention, automated means (e.g., operating in an environment such as the exemplary operating environment of FIG. 1) is used to identify a comparable brand drug for the generic drug to be priced according to a method of this invention. For example, referring to the embodiment of the invention illustrated at FIG. 2, a database of generic drugs and brand drugs may be provided, a user may input information about the generic drug 200 (e.g., the name, dosage form, strength, active ingredient, or other identifying information), and a program executed on the computer may be used to identify a comparable brand drug for the generic drug based on pharmaceutical equivalence, bioequivalence, and/or therapeutic class 202.

Figure 3:
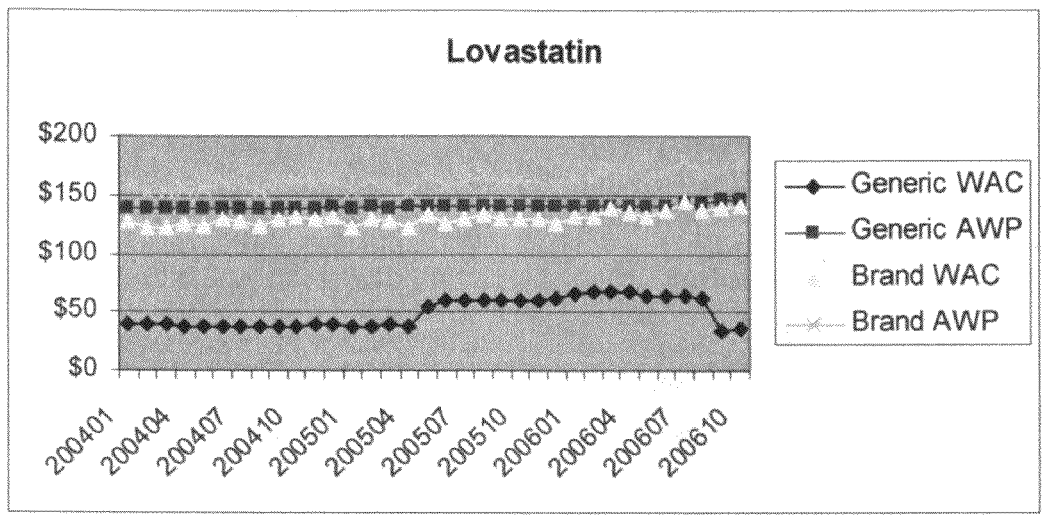
FIG. 3 is a graph illustrating benchmark values of Lovastatin over time.
Figure 4:
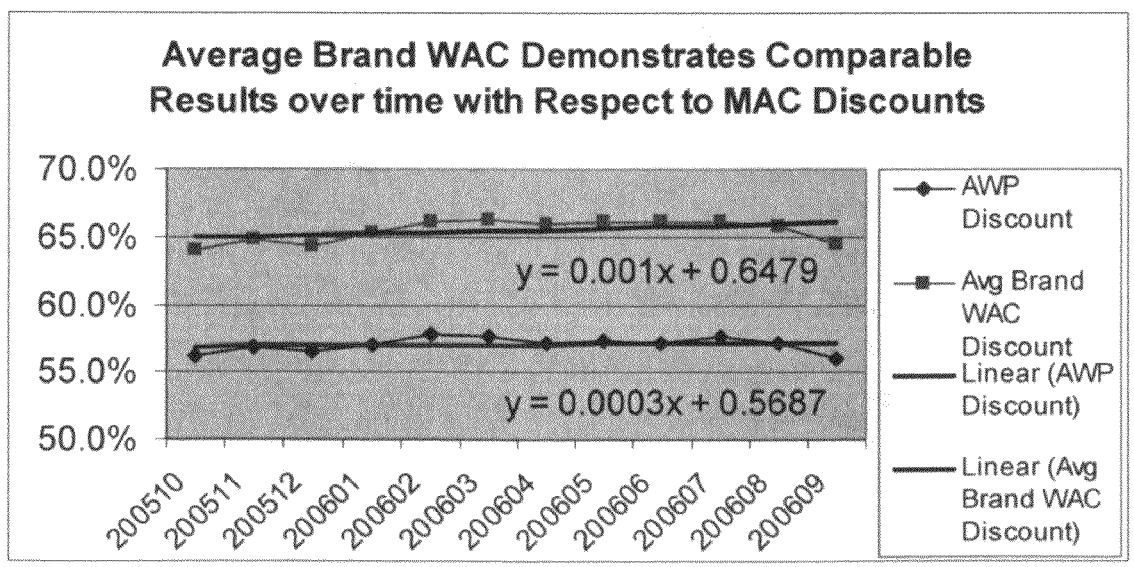
FIG. 4 is a graph illustrating AWP and average brand WAC over time.

Methods of determining a price of a generic drug according to an embodiment of this invention further comprise identifying a comparable brand drug value for the comparable brand drug. 204 As illustrated on the charts of FIG. 3 and FIG. 4, the inventor has discovered that a Brand WAC of a comparable brand drug may provide a stable benchmark for pricing a generic drug and can be used to create a benchmark for use in the novel, innovative methods of this invention. Accordingly, a preferred comparable brand drug value of a comparable brand drug for use in a method of this invention is a wholesale acquisition cost of the comparable brand drug. However, other measures of the value of a comparable brand drug may be used according to a method of this invention, such as an average wholesale price or an average manufacturer's price of the comparable brand drug.

A comparable brand drug value may be identified for a generic drug to be priced according to a method of this invention by one or more skilled individuals. A group of skilled individuals may work together to identify a comparable brand drug value for a comparable brand drug by consensus. In a preferred computer-implemented embodiment of this invention, automated means is used to identify a comparable brand drug value for the identified comparable brand drug. For example, a database of drugs and brand drug values may be provided, and a program executed on the computer may be used to identify a comparable brand drug value for the identified comparable brand drug.

In a preferred embodiment of this invention, more than one comparable brand drug value is identified for each identified comparable brand drug. Under a preferred embodiment, the Brand WAC of all package sizes of the identified comparable brand drug will be identified as comparable brand drug values for the comparable brand drug. For example, a Brand WAC is usually provided for each available strength and package size of a drug, i.e., each brand drug will have a Brand WAC at its NDC (for "national drug code") 11 level. In this preferred embodiment, each Brand WAC provided for a comparable brand drug that is identical through its NDC 9 level is identified as a comparable brand drug value according to a method of this invention.

In certain embodiments of methods of this invention, other or additional comparable brand drug values (e.g., Brand WACs) may be identified. For example, the identified comparable brand drug may be identified as a brand drug that contains the same therapeutic moiety of the generic drug, but in a different amount. Furthermore, depending upon the desired level of specificity, the identified comparable brand drug may be identified as the brand drug that contains the same active ingredient as the generic drug to be priced according to a method of this invention, without regard to the amount of the active ingredient. Thus, in this example, identified comparable brand drug values may be the wholesale acquisition costs provided for each available strength and dosage of the identified comparable brand drug.

Having identified one or more comparable brand drug values for the identified comparable brand drug, methods of this invention further comprise calculating a benchmark value for the generic drug based on the identified comparable brand drug value or values. 206 If a single comparable brand drug value is identified, it may be used as a benchmark value for the generic drug. Thus, "calculating" a benchmark value may simply refer to selecting the identified comparable brand drug value as the benchmark value.

In other embodiments, calculating a benchmark value of a generic drug to be priced according to a method of this invention will include further analysis and/or manipulation of the previously-identified comparable brand drug value or values. For example, if more than one comparable brand drug value is identified, it may be appropriate to mathematically manipulate, combine, or otherwise consider together (collectively "mathematically combine"), e.g., arithmetically, graphically, algebraically, or otherwise, the comparable brand drug values to establish part or all of a benchmark value. Thus, a benchmark value of a generic drug could simply be the average of the identified comparable brand drug values. Some or all of the identified comparable brand drug values could be weighted (e.g., multiplied by numbers less than or greater than 1) and the resulting weighted comparable brand drug values averaged. Other values, such as the generic wholesale acquisition cost of the generic drug to be priced according to a method of this invention, could be included along with one or more comparable brand drug values for purposes of calculating a benchmark value.

In a preferred embodiment of determining a price of a generic drug according to a method of this invention, each Brand WAC provided for a comparable brand drug that is identical through its NDC 9 level is identified as a comparable brand drug value according to a method of this invention, and the benchmark is calculated as the average per unit (e.g., per tablet, capsule, or other dosage unit) value of the comparable brand drug, based on the identified comparable brand drug values.

If the identified comparable brand drug contains a different amount of active ingredient than the generic drug to be priced according to a method of this invention (or is identified without regard to amount of active ingredient), a benchmark could be calculated as the average per unit of active ingredient (e.g., per milligram), based on the identified comparable brand drug values.

In a preferred computer-implemented embodiment of this invention, automated means is used to calculate a benchmark value for the generic drug to be priced according to a method of this invention, based on the identified comparable brand drug value or values. For example, a program executed on a computer used in a method of this invention may be used to perform the calculation of the benchmark value.

A calculated benchmark value can be used to determine the price of a generic drug, according to a method of this invention. 208 In a preferred computer-implemented embodiment of this invention, automated means is used to determine the price of a generic drug according to a method of this invention, based on the identified comparable brand drug value or values. For example, a program executed on the computer used in a method of this invention may be used to determine the price of a generic drug. In a computer-implemented method of this invention, a determined generic drug price is provided 210, e.g., the determined generic drug price is provided to a user by causing the price to be displayed on a screen, to be printed, to be provided as sound the user is capable of hearing, or to otherwise be provided in a manner that can be observed by a user, directly or indirectly.

According to certain embodiments of the present invention, a discount factor, a rebate factor, a dispensing fee factor, a co-payment factor, and/or other information relevant to pricing a generic drug may be provided and/or received. Such relevant pricing information may be provided and/or received based on a specific payee, class of payee, and/or otherwise tailored for the specific purpose or purposes for which the price of a generic drug will be determined according to a method of this invention. As will be understood by those with skill in the art, such factors and/or relevant pricing information may be received and/or provided in the form of a fixed amount, a percentage, or in any other form known in the art.

Using a method of this invention, the price of a generic drug may be determined as follows:

Generic drug: 20 mg tablets of lovastatin
Identified comparable brand drug: Mevacor (20 mg, identified independent of package size)
Identified comparable brand drug value: wholesale acquisition cost of 20 mg Mevacor
Calculation of benchmark value (Brand WACs are representative, not actual):

| | |
|---|---|
| Per unit Brand WAC for Mevacor at first NDC 9 level: | $7 |
| Per unit Brand WAC for Mevacor at second NDC 9 level: | $10 |
| Per unit Brand WAC for Mevacor at third NDC 9 level: | $13 |
| Average Brand WAC (per unit) = "Benchmark Value": | $10 |

Determining the price of a 30 unit supply of lovastatin based on the benchmark value:

| | |
|---|---|
| Benchmark value: | $10 |
| Benchmark value per 30 unit supply ($10 × 30): | $300 |
| Discount factor: | −50% (i.e., −$150) |
| Dispensing fee factor: | +$2 |
| Net payee rate: | $152 |
| Less co-payment factor: | −$10 |
| Net price of 30 day supply of generic drug (lovastatin): | $142 |

Innovative use of a benchmark for pricing a generic drug that comprises one or more wholesale acquisition costs of an identified comparable brand drug for generic drug, according to an embodiment of the present invention, creates a stable, predictable benchmark for pricing that generic drug, with a trend very similar to that historically found using the AWP for such generic drug. In some instances, this benchmark appears to be a more predictable benchmark than if the WACs for the generic drugs of the particular compound and strength were also used in calculating the average. Thus, a benchmark created using the wholesale acquisition costs of one product (e.g., an identified comparable brand drug), unpredictably, is a stable predictor to use for benchmark pricing of another product (e.g., the generic drug selected for pricing according to an embodiment of the present invention).

Although the invention has been described with reference to specific embodiments, it will be understood by those skilled in the art that various changes may be made without departing from the spirit or scope of the invention. Accordingly, the disclosure of embodiments of the invention is intended to be illustrative of the scope of the invention and is not intended to be limiting. For example, to one of ordinary skill in the art, it will be readily apparent that the method discussed herein may be implemented in a variety of embodiments, and that the foregoing discussion of certain of these embodiments does not necessarily represent a complete description of all possible embodiments. Rather, the detailed description of the invention and the figures disclose at least one preferred embodiment of the invention, and may disclose alternative embodiments of the invention

I claim:
1. A method comprising:
identifying, on a processor, a comparable brand prescription drug to a generic prescription drug, the generic prescription drug being at least pharmaceutically comparable to the first comparable brand prescription drug;
identifying, on the processor, a first drug availability of the comparable brand prescription drug, the first drug availability being associated with a first national drug code (NDC) 11 level;
identifying, on the processor, a second drug availability of the comparable brand prescription drug, the second drug availability being associated with a second national drug code (NDC) 11 level, the second NDC 11 level being different than the first NDC 11 level, the first drug availability and the second drug availability being identical through a NDC 9 level;

identifying, on the processor, a wholesale acquisition cost (WAC) of the first availability of the comparable brand prescription drug;

identifying, on the processor, the WAC of the second availability of the comparable brand prescription drug;

calculating, on the processor, a benchmark value for the generic prescription drug based on the WAC of the first availability and the second availability of the comparable brand prescription drug; and accessing, on the processor, a discount factor, a dispensing fee factor, a net payee rate, and a copayment factor;

determining, on the processor, a reimbursement price of the generic prescription drug based on the benchmark value, the discount factor, the dispensing fee factor, the net payee rate, and the copayment factor, the reimbursement price being a price of the generic prescription drug associated with a PBM, the reimbursement price being a different amount than an out-of-pocket price paid by the participant for the generic prescription drug.

2. The method of claim 1, wherein determining the price of the generic prescription drug comprises:
determining, on the processor, a per unit price of the generic prescription drug based on the benchmark value.

3. The method of claim 1, wherein determining the reimbursement price of the generic prescription drug comprises:
determining, on the processor, a per measure of active ingredient of the generic prescription drug based on the benchmark value.

4. The method of claim 1, further comprising:
determining placement of the generic prescription drug in a step therapy treatment protocol based on a determination of the reimbursement price of the generic prescription drug.

5. The method of claim 1, further comprising:
determining whether to include the generic prescription drug on a formulary is based on a determination of the reimbursement price of the generic prescription drug.

6. The method of claim 1, further comprising:
receiving identifying information regarding the generic prescription drug,
wherein identification of the comparable brand prescription drug is based on receipt of the identifying information.

7. The method of claim 1, wherein the benchmark value includes an average per unit benchmark value.

8. The method of claim 1, wherein the benchmark value includes an average per unit of active ingredient benchmark value.

9. The method of claim 1, wherein the generic prescription drug is a drug for which there is no current patent protection in a relevant jurisdiction.

10. The method of claim 1, wherein the reimbursement price of the generic prescription drug based on the benchmark value is different than the average wholesale price of the generic prescription drug.

11. The method of claim 1, wherein the generic prescription drug is pharmaceutically equivalent to the first comparable brand prescription drug.

12. The method of claim 1, wherein calculating the benchmark value comprises:
calculating an average per unit of ingredient benchmark value for the generic prescription drug based on the WAC of the first availability and the second availability of the comparable brand prescription drug,
wherein determination of the reimbursement price of the generic prescription drug is based on the average per unit of ingredient benchmark value.

13. The method of claim 1, further comprising:
generating a display including the reimbursement price of the generic prescription drug.

14. The method of claim 1, wherein the reimbursement price includes a reimbursement rate paid by a plan sponsor to the PBM for dispensing of the generic prescription drug to a participant, the participant being in a prescription drug plan associated with the plan sponsor.

15. The method of claim 1, wherein the reimbursement price includes a drug fill rate paid by a PBM to a retail pharmacy for dispensing of the generic prescription drug to a participant, the participant being in a prescription drug plan associated with a plan sponsor.

16. A non-transitory computer readable medium comprising instructions, which when implemented by one or more processors perform the following operations:
identify a comparable brand prescription drug to a generic prescription drug, the generic prescription drug being at least pharmaceutically comparable to the comparable brand prescription drug;
identify a first drug availability of the comparable brand prescription drug, the first drug availability being associated with a first national drug code (NDC) 11 level;
identify a second drug availability of the comparable brand prescription drug, the second drug availability being associated with a second national drug code (NDC) 11 level, the second NDC 11 level being different than the first NDC 11 level, the first drug availability and the second drug availability being identical through a NDC 9 level;
identify a wholesale acquisition cost (WAC) of the first availability of the comparable brand prescription drug;
identify the WAC of the second availability of the comparable brand prescription drug;
calculate a benchmark value for the generic prescription drug based on the WAC of the first availability and the second availability of the comparable brand prescription drug; and
access a discount factor, a dispensing fee factor, a net payee rate, and a copayment factor;
determine a reimbursement price of the generic prescription drug based on the benchmark value, the discount factor, the dispensing fee factor, the net payee rate, and the copayment factor, the reimbursement price being a price of the generic prescription drug associated with a PBM the reimbursement price being a different amount than an out-of-pocket price paid by the participant for the generic prescription drug.

* * * * *